United States Patent [19]
Villaescusa et al.

[11] 3,944,575
[45] Mar. 16, 1976

[54] ARYL ETHER COMPOUNDS AND THEIR SYNTHESIS

[75] Inventors: Frank W. Villaescusa; John G. Breland, both of Colorado Springs, Colo.; Fred E. Arnold, Centerville, Ohio

[73] Assignee: The United States of America as represented by the Secretary of the Air Force, Washington, D.C.

[22] Filed: May 30, 1974

[21] Appl. No.: 474,560

[52] U.S. Cl. ............... 260/395; 260/390; 260/571; 260/590 R; 260/607 A; 260/609 F; 260/613 R
[51] Int. Cl.² ................... C09B 11/06; C09B 11/10
[58] Field of Search............ 260/571, 613 R, 607 A, 260/390, 395, 590, 609 F

[56] References Cited
UNITED STATES PATENTS
3,654,364  4/1972  Meckel et al. ...................... 260/571

OTHER PUBLICATIONS

Index Chemicus 28, 89702 (1968).

Balcom et al., J. Am. Chem. Soc., 75, 4334 (1953).

*Primary Examiner*—D. Horwitz
*Attorney, Agent, or Firm*—Joseph E. Rusz; Cedric H. Kuhn

[57] ABSTRACT

Tetranitro aryl ether compounds are prepared by aromatic nucleophilic substitution of various aryl diols with 4-fluoro-1,2-dinitrobenzene. By reducing the nitro moieties of the tetranitro compounds, tetraamino aryl ether compounds are obtained. These latter compounds are useful as monomers in preparing thermally stable polymers having good solubility parameters.

14 Claims, No Drawings

ARYL ETHER COMPOUNDS AND THEIR SYNTHESIS

RIGHTS OF THE GOVERNMENT

The invention described herein may be manufactured and used by or for the Government of the United States for all governmental purposes without the payment of any royalty.

FIELD OF THE INVENTION

This invention relates to aryl ether compounds and to a process for their synthesis. In one aspect it relates to aromatic tetraamino ether monomeric compositions.

BACKGROUND OF THE INVENTION

Workers in the field are constantly searching for polymeric materials having high temperature properties, i.e., the ability to retain their physical and chemical characteristics as well as their dimensional stability at elevated temperatures of the order of 500°C and above. Regarding problems being encountered or anticipated in the applications of high temperature nonmetallic materials, the aromatic heterocyclic polymers have been found to be particularly useful in a variety of aerospace applications. For example, such polymers can be used on the skin or leading edges of high speed aircraft, on the nose cone and heat shields of atmospheric escape and re-entry vehicles, in the fabrication of various rocket engine components, and the like. Unfortunately, the fused and highly aromatic nature of these ring systems, which give them their exceptional stability, tends to render them intractable.

It is an object of the present invention, therefore, to provide new and improved tetrafunctional amino monomers which can be used in the preparation of thermally stable polymers having improved solubility parameters.

Another object of the invention is to provide tetranitro aryl ether compounds which are employed as intermediates in the synthesis of the amino monomers.

A further object of the invention is to provide a process for synthesizing the tetranitro aryl ether compounds.

A still further object of the invention is to provide a process for synthesizing the tetrafunctional amino monomers.

Other objects and advantages of the invention will become apparent to those skilled in the art upon consideration of the accompanying disclosure.

SUMMARY OF THE INVENTION

The present invention resides in an arylene-oxy compound having the following formula:

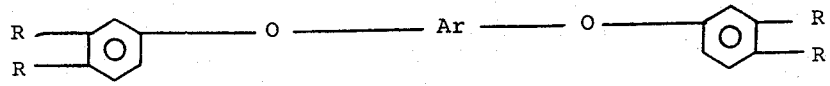

wherein R is NO₂, NH₂ or NH₃Cl and Ar is a divalent aromatic radical. Examples of divalent aromatic radicals include the following:

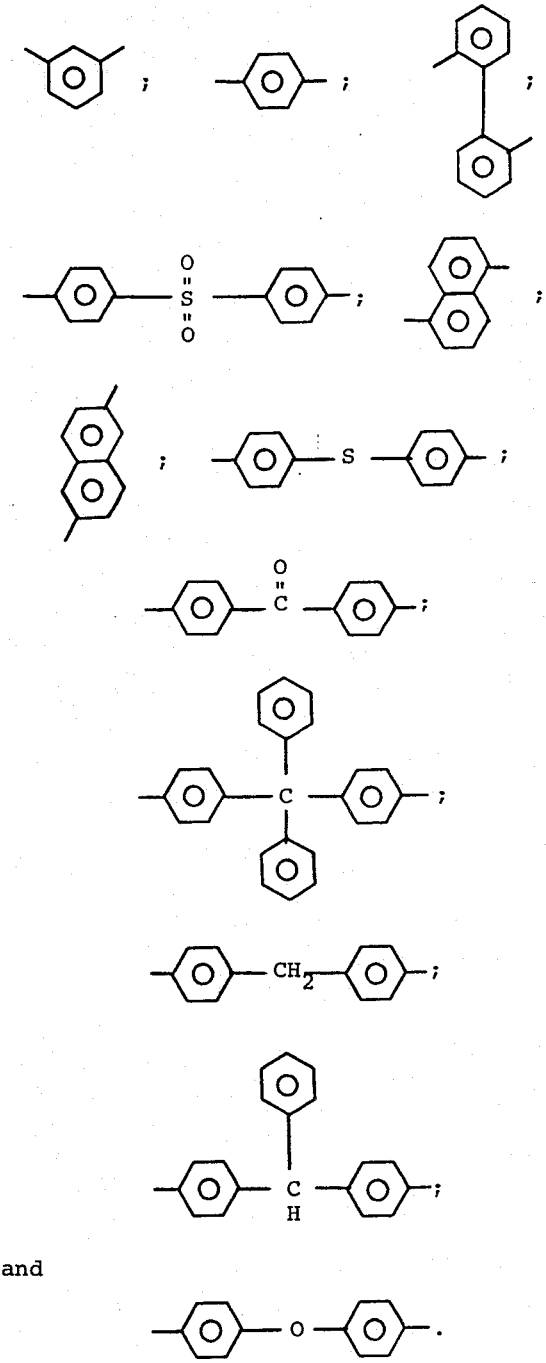

and

When R is NO₂, the compounds represented by the above formula are tetranitro aryl ether compounds which are the intermediates used in preparing the tetrafunctional amino monomers of this invention. The monomers themselves are defined by the formula when R is NH₂ or NH₃Cl. As seen from the foregoing structural formula, the monomers contain aromatic ether linkages. When the monomers undergo a condensation reaction with a suitable comonomer, the ether linkages impart several sites for bond rotation within the polymer chains, thus improving solubility parameters. As a result the polymers are rendered more processable, thereby alleviating the problem of intractability of conventional aromatic polymers. The monomers can be polymerized with conventional comonomers so as to prepare benzimidazo, quinoxaline, phenylquinoxaline and pyrone polymers. In particular, the monomers are useful in preparing benzimidazobenzophenanthroline polymers by their polycondensation with multifunctional aromatic carboxylic acids, such as 1,4,5,8-naphthalene tetracarboxylic acid, as disclosed in our copending application Ser. No. 474,562, filed on 5-30-74, now U.S. Pat. No. 3,925,311. The disclosure of this copending application is incorporated herein by reference.

In one embodiment, the present invention resides in a process for preparing the tetranitro aryl ether compounds which are intermediates for synthesizing the tetrafunctional amino monomers. Thus, the compounds are synthesized by aromatic nucleophilic substitution of various aryl diols with 4-fluoro-1,2-dinitrobenzene. The reaction involved is illustrated by the following equation:

Although stoichiometric amounts of the 4-fluoro-1,2-dinitrobenzene and the aryl diol can be used, it is usually preferred to employ a molar excess of the former compound. Thus, the mol ratio of 4-fluoro-1,2-dinitrobenzene to aryl diol usually falls in the range of about 2 to 5, preferably 2 to 3, to 1. It is generally preferred to use a slight molar excess of the base, based on the amount of the aryl diol. Thus, the mol ratio of the base to the aryl diol is usually in the range of about 1.0 to 1.5 to 1.

At the end of the reaction period, the reaction mixture is poured into a dilute acid solution, thereby precipitating a crude product from solution. Examples of suitable acids include hydrochloric acid, formic acid, and acetic acid. After recovery of the crude product, e.g., by decantation of the aqueous phase or by extraction with methylene chloride, it is then purified so as to obtain a high purity product.

Purification of the crude product can be accomplished by any suitable means. In one procedure, the crude product is dissolved in chloroform after which the solution is washed successively with dilute hydro-

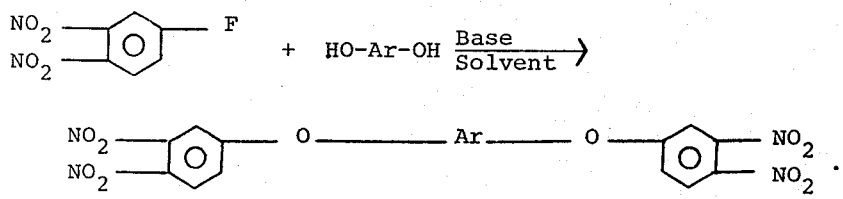

In this equation, Ar is as indicated above. Examples of aryl diols which can be employed include 1,3-dihydroxybenzene; 1,4-dihydroxybenzene; 1,1'-dihydroxybiphenyl; 4,4'-dihydroxydiphenylsulfone; 1,5-dihydroxynaphthalene; 2,6-dihydroxynaphthalene; 4,4'-dihydroxydiphenylsulfide; 4,4'-dihydroxybenzophenone; bis(4-hydroxyphenyl)diphenylmethane; 4,4'-dihydroxydiphenylether; and 4,4'-dihydroxydiphenylmethane.

As depicted in the above equation, the reaction is conducted in a reaction medium, which is a solvent for the reactants and the reaction product, in the presence of a base. Furthermore, the reaction is carried out in an inert atmosphere, such as that provided by nitrogen, helium, argon, and the like. The temperature employed usually ranges from about −5°C to 150°C, and the reaction period is generally from about 1 to 24 hours.

Examples of solvents that can be employed include pyridine, N,N'-dimethylacetamide; dimethylsulfoxide, dimethylformamide, hexamethylphosphoramide, tetramethylsulfone, N-methyl-pyrrolidone, and the like. It is often preferred to utilize pyridine as the solvent.

In general, inorganic or organic bases can be used in the process. Exemplary compounds include sodium hydride, lithium hydride, calcium hydride, sodium hydroxide, potassium hydroxide, lithium hydroxide, barium hydroxide, sodium methoxide, sodium ethoxide, potassium tert-butoxide, and the like.

chloric acid, saturated sodium bicarbonate or sodium chloride solution, and water. After drying over magnesium sulfate, the solvent is evaporated, thereby giving a product in the form of an oil. The oil is then chromatographed on silica gel by elution with hexane, benzene, ethyl acetate, or mixtures thereof. The oil is then dissolved in an organic solvent, such as ethanol, benzene, hexane, cyclohexane, acetone or mixtures thereof, after which the product is allowed to crystallize from solution. It is often advantageous to carry out more than one crystallization in order to increase the purity of the product. In another procedure for purifying the product, the crude product is washed with water and then vacuum dried to yield a solid material. After dissolving this material in boiling tetrahydrofuran, the resulting solution is treated with charcoal and filtered. The solution is then reheated to boiling, and ethanol is slowly added. Storage of the resulting mixture at a subzero temperature, e.g., about −10° to −20°C, for about 12 to 24 hours, yields a purified product. Further purification of the product can be obtained by following the above-described crystallization procedure.

In another embodiment, the present invention resides in a process for converting the intermediate tetranitro aryl ether compounds to the aromatic tetraamino monomers. This is accomplished by reduction of the intermediate with hydrazine or hydrazine hydrate in the presence of a catalyst as illustrated by the following equation:

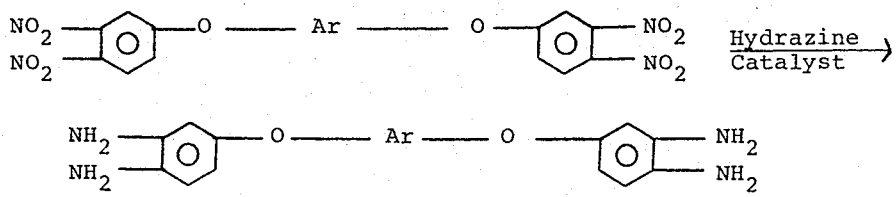

In the above equation, Ar is as indicated hereinabove. When it is desired to obtain a tetraamino hydrochloride as the product, the tetraamino compound is contacted with concentrated hydrochloric acid. Because the tetraamino hydrochlorides are often more stable than the tetraamines, it is frequently preferred to use the former compounds as monomeric materials.

The reduction reaction is conducted under a blanket of an inert gas such as those mentioned hereinbefore. In one procedure, the intermediate, i.e., the tetranitro aryl ether compound, is dissolved in a solvent therefor, e.g., an alcohol such as methanol, ethanol, isopropanol, or tert-butanol. Catalyst is then added to the solution followed by addition of hydrazine or hydrazine hydrate. The solution is thereafter heated under reflux conditions for a period of about 2 to 24 hours. At the end of this period, the reaction mixture is cooled, e.g., to about 5° to 10°C, and filtered under an inert gas. The solvent is then removed by vacuum distillation to provide the tetraamine monomer of this invention. In a preferred procedure, the cooled reaction mixture is filtered into cold concentrated hydrochloric acid. The resulting precipitate of hydrazine hydrochloride and tetraamine hydrochloride is recovered, e.g., by filtration, partially dried, and then dissolved in water. A concentrated ammonium hydroxide, sodium hydroxide, sodium carbonate or sodium bicarbonate solution is added to the resulting solution, thereby precipitating the desired tetraamino aryl ether product. After separation of the product as by decantation or filtration, it is dried under a vacuum. By dissolving the product in an organic solvent, such as ethanol, tetrahydrofuran, benzene, hexane, cyclohexane, or acetone, either alone, in admixture with one another, or in admixture with water, and then allowing the product to crystallize from solution, a highly purified product can be obtained. By repeating the dissolution and crystallization procedure, the purity of the product can be increased.

The catalyst used in the reduction reaction consists essentially of palladium, platinum or Raney nickel on a charcoal support. The catalyst contains about 5 to 10 weight percent of the metal. The amount of catalyst used generally ranges from about 0.1 to 5 weight percent, based upon the weight of the intermediate. Either anhydrous hydrazine or hydrazine hydrate can be utilized as the reducing agent. As to the amount used, the mol ratio of hydrazine to the intermediate is at least 4 to 1. It is usually preferred to use an excess of the hydrazine, e.g., 4.1 to 6 mols of the hydrazine per mol of the intermediate.

A more complete understanding of the invention can be obtained by referring to the following illustrative examples which are not intended, however, to be unduly limitative of the invention.

EXAMPLE I a. 1,3-Bis(3,4-dinitrophenoxy)benzene 1,3-Dihydroxybenzene (2.20 g, 20 mmoles) was added to a 200 ml flask equipped with a nitrogen inlet, magnetic stirrer and thermometer and containing 1.90 g of a 57 percent dispersion of sodium hydride in 100 ml of dry pyridine. After the initial evolution of hydrogen subsided, the resulting suspension of sodium recorcinate was heated at 50°C for 1 hour, and then chilled to −5°C with a salt-ice bath. Solid 4-fluoro-1,2-dinitrobenzene (9.16 g, 60 mmoles) was added all at once to the flask in the salt-ice bath which was allowed to warm overnight to room temperature. The reaction mixture was poured into 2N HCl (400 ml), and the aqueous phase was decanted from the resulting red tar. The tar was taken up in chloroform (300 ml), washed 5 times with 100 ml of 2N HCl, followed by washing with saturated NaHCO$_3$ solution (100 ml) and water, and dried over MgSO$_4$. Evaporation of solvent yielded 11.98 g of red oil which was chromatographed on silica gel (180 g) by elution with hexane-benzene mixtures. The yield of the desired product in the form of a yellow solid was 6.50 g (57 percent). Two recrystallizations from ethanol provided an analytical sample (melting point 107°–108.5°C).

Analysis - Calc'd for $C_{18}H_{10}N_4O_{10}$ (percent): C, 48.88; H, 2.28; N, 12.67. Found (percent): C,49.27; H,2.28; N,12.70.

b. 1,3-Di(3,4-diaminophenoxy)benzene hydrochloride

In a 1 liter 3-neck flask equipped with a magnetic stirrer, heating mantle, reflux condenser, addition funnel and gas dispersion tube, a suspension of 1,3-bis(3,4-dinitrophenoxy)benzene (7.00 g, 0.016 mmole) in absolute ethanol (600 ml) was heated under reflux for one hour with nitrogen bubbling below the liquid surface. Heating was terminated and after boiling had subsided, 10 percent palladium on charcoal (0.80 g) was added, followed by dropwise addition of hydrazine hydrate (16 ml). The reaction was heated under reflux for 3 hours, cooled to 7°C, and suction filtered through Celite filter aid under nitrogen. The solvent was removed in vacuo to produce the tetraamine as brown solid which was dissolved in tetrahydrofuran (200 ml), followed by addition of concentrated hydrochloric acid (200 ml). The resulting purple precipitate was collected and, while still wet, dissolved in water (100 ml), heated with Norit purified charcoal, and filtered. Addition of concentrated hydrochloric acid (200 ml) and storage overnight at −15°C yielded the tetraamino hydrochloride product (4.68 g, 62 percent) as a pink solid (melting point 232°–6°C).

Analysis - Calc'd for $C_{18}H_{22}N_4O_2Cl_4$ (percent): C,46.18; H,4.74; N,11.97. Found (percent): C,45.95; H,4.38; N,11.82.

EXAMPLE II a. 2,2'-Bis(3,4-dinitrophenoxy)biphenyl

A 57 percent dispersion of sodium hydride in oil (6.3 g, 0.15 mole) was added to a stirred solution of 4-fluoro-1,2-dinitrobenzene. A solution of 1,1'-dihydroxybiphenyl (0.6 g, 0.046 mmole) in pyridine (50 ml) was added dropwise over a 45 minute period. Reaction temperature was maintained below 40°C by periodic use of an ice bath. The reaction mixture was stirred for 18 hours, poured into 2N HCl (800 ml), and extracted with methylene chloride. The extract was washed with 2N HCl, water, and saturated sodium chloride solution, and dried over magnesium sulfate. Evaporation of the solvent yielded 26.3 g of red oil. Chromatography on silica gel with hexane-benzene mixtures produced 16.2 g (67 percent) of the desired product. The analytical sample was obtained by recrystallization of a portion of the product from a cyclohexane-benzene mixture.

Analysis - Calc'd for $C_{24}H_{14}N_4O_{10}$ (percent): C,55.61; H,2.72; N,10.81. Found (percent): C,55.58;

H,2.78; N,10.73 b. 2,2'-Bis(3,4-diaminophenoxy)biphenyl

A stirred mixture of 2,2'-bis(3,4-dinitrophenoxy)biphenyl (22.0 g, 0.0425 mole) and 10 weight percent palladium on charcoal (2.2 g) in absolute ethanol (500 ml) was heated to reflux under nitrogen, and a solution of hydrazine hydrate (43 ml) in ethanol (100 ml) was added dropwise over a period of 40 minutes. The reaction mixture was heated at reflux for 17 hours, chilled in an ice bath, and suction filtered through Celite filter aid into one liter of stirred, cold, concentrated hydrochloric acid. The resulting precipitate of hydrazine hydrochloride and desired tetraamine hydrochloride was collected, partially dried and dissolved in water (1 liter). Concentrated ammonium hydroxide solution (300 ml) was added and the resulting precipitate collected and vacuum dried to produce 14.9 g (88 percent) of 2,2'-bis(3,4-diaminophenoxy)biphenyl). A portion of the product was recrystallized from ethanol-water to provide an analytical sample (melting point 172°–174°C).

Analysis - Calc'd for $C_{24}H_{22}N_4O_2$ (percent): C,72.34, H,5.57; N,14.06. Found (percent): C,72.12; H,5.42; N,13.83.

EXAMPLE III a. 1,5-Bis(3,4-dinitrophenoxy)naphthalene 1,5-Dihydroxynaphthalene (3.20 g, 0.020 mmole) was added to a stirred suspension of sodium hydride (1.68 g of a 57 percent dispersion) in dry pyridine (100 ml). The mixture was heated under nitrogen at 50°C for 1 hour, chilled to −2°C, and 1,2-dinitro-4-fluorobenzene (11.20 g, 0.060 mole) added all at once. After stirring for 3 hours at −5°C, the reaction mixture was poured into 2N HCl (500 ml) and the brown precipitate collected, washed with water, and vacuum dried to yield 10.7 g of pale brown solid. The crude product was dissolved in boiling tetrahydrofuran (900 ml), treated with charcoal, filtered, and the volume reduced by evaporation of solvent to 350 ml. The solution was reheated to boiling and 95 percent ethanol (200 ml) was slowly added. Storage at −15°C for 18 hours produced 6.22 g (63 percent) of the desired product as a yellow solid (melting point 224°–228°C). An analytical sample (melting point 231°–232°C) was obtained by recrystallizing a small portion of the product several times from tetrahydrofuran-ethanol.

Analysis - Calc'd for $C_{22}H_{12}N_4O_{10}$ (percent): C,53.67; H,2.46; N,11.38. Found (percent): C,54.09; H,2.35; N,11.21.

b. 1,5-Bis(3,4-diaminophenoxy)naphthalene

A stirred mixture of 1,5-bis(3,4-dinitrophenoxy)naphthalene (6 g, 0.0122 mole) and 10 percent palladium on charcoal (0.6 g) in absolute ethanol (300 ml) was heated to reflux under nitrogen. A solution of hydrazine hydrate (8 ml) in ethanol (30 ml) was added dropwise over a period of 40 minutes. The reaction mixture was heated at reflux for 6 hours, chilled in an ice bath, and suction filtered through Celite filter aid into one liter of stirred, cold, concentrated hydrochloric acid. The resulting precipitate of hydrazine hydrochloride and the desired tetraamino hydrochloride was collected, partially dried, and dissolved in water (300 ml). Concentrated ammonium hydroxide solution (60 ml) was added and the resulting precipitate collected and vacuum dried to produce 4.5 g (90 percent) of the desired 1,5-bis(3,4-diaminophenoxy)naphthalene. Recrystallization from benzene gave a white product (melting point 230°–231°C).

Analysis - Calc'd for $C_{22}H_{20}N_4O_2$ (percent): C,70.94; H,5.41; N,14.46. Found (percent): C,71.30; H,5.40; N,14.37.

EXAMPLE IV a. 4,4'-Bis(3,4-dinitrophenoxy)diphenyl sulfone 4,4'-Dihydroxydiphenyl sulfone (5 g, 0.020 mol) was added under nitrogen to a stirred suspension of sodium hydride (57 percent dispersion in oil, 1.70 g, 0.040 mol) in pyridine (100 ml). After stirring for 30 minutes, solid 4-fluoro-1,2-dinitrobenzene (9.2 g, 0.060 mol) was added all at once. After stirring at room temperature for 5 hours, the reaction mixture was poured into 2N HCl. The resulting red tar was taken up in acetone and precipitated with water to yield a red solid (12.0 g). Chromatography on silica gel with hexane-ethyl acetate mixtures yielded 8.0 g (69 percent) of crude product. Several recrystallizations from acetone-hexane mixture gave a purified product (melting point 197°–198.5°C).

Analysis - Calc'd for $C_{24}H_{14}N_4O_{12}S$ (percent): C,49.49; H,2.42; N,9.62; S,5.50. Found (percent): C,49.60; H,2.40; N,9.52; S,5.65.

b. 4,4'-Bis(3,4-diaminophenoxy)diphenyl sulfone

A stirred mixture of 4,4'-bis(3,4-dinitrophenoxy)diphenyl sulfone (1.6 g, 2.74 mmoles) and 10 percent palladium on charcoal (0.15 g) in absolute ethanol (150 ml) was heated to reflux under nitrogen. A solution of hydrazine hydrate (5 ml) in ethanol (30 ml) was added dropwise over a period of 10 minutes. The reaction mixture was heated at reflux for 16 hours, chilled in an ice bath, and suction filtered through Celite filter aid into stirred, cold, concentrated hydrochloric acid (300 ml). The resulting precipitate of hydrazine hydrochloride and the tetraamino hydrochloride was collected, vacuum dried, and dissolved in water (100 ml). Addition of concentrated ammonium hydroxide (15 ml) produced 0.8 g (63 percent) of the desired product 4,4'-bis(3,4-diaminophenoxy)diphenyl sulfone (melting point 105°–110°C).

Analysis - Calc'd for $C_{24}H_{22}N_4O_4S$ (percent): C,62.32; H,4.79; N,12.11; S,6.93. Found (percent): C,61.95; H,4.30; N,11.92; S,6.54.

As will be evident to those skilled in the art, modifications of the present invention can be made in view of the foregoing disclosure. Such modifications come within the spirit and scope of the invention.

We claim:

1. As a new composition of matter, an arylene-oxy compound having the following formula:

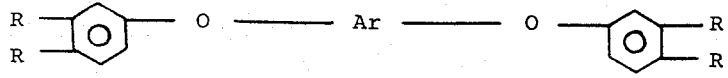

where R is NO₂, NH₂ or NH₃Cl, and wherein Ar is

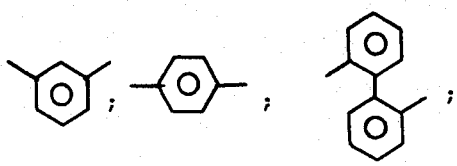

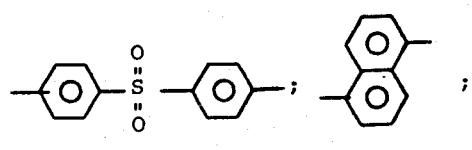

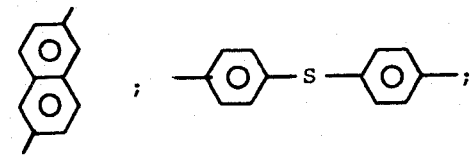

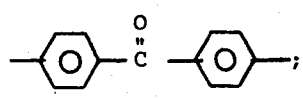

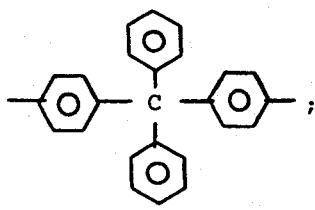

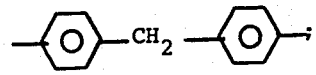

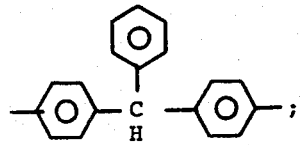

or

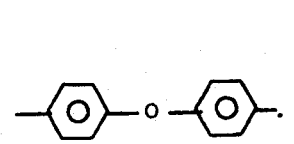

2. The composition of claim 1 in which R is NO₂.
3. The composition of claim 1 in which R is NH₂.
4. The composition of claim 1 in which R is NH₃Cl.
5. The composition of claim 1 in which Ar is

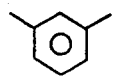

6. The composition of claim 1 in which Ar is

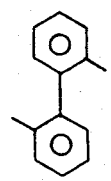

7. The composition of claim 1 in which Ar is

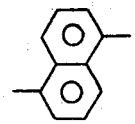

8. The composition of claim 1 in which Ar is

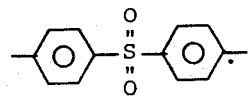

9. The composition of claim 1 in which Ar is

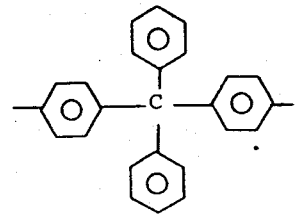

10. A process for preparing a tetranitro aryl ether compound which comprises reacting 4-fluoro-1,2-dinitrobenzene with an aryl diol having the following formula: HO-Ar-OH, wherein Ar is

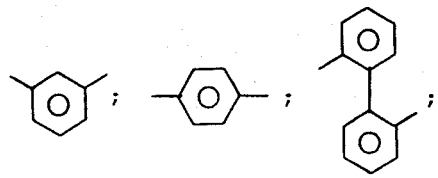

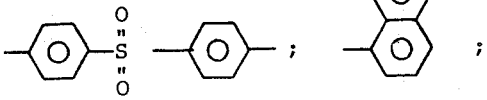

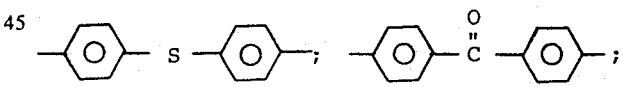

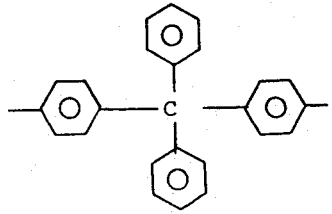

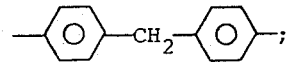

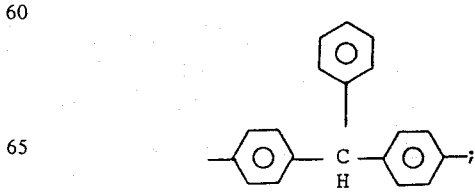

or

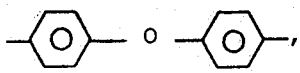

the reaction being conducted in a solvent under an inert atmosphere and in the presence of an organic or inorganic base; and recovering the tetranitro aryl ether compound.

11. The process according to claim 10 in which the mol ratio of 4-fluoro-1,2-dinitrobenzene to the aryl diol is in the range of about 2 to 5 to 1; the mol ratio of the base to the aryl diol is in the range of about 1.0 to 1.5 to 1; and the reaction is conducted at a temperature ranging from about −5°C to 150°C for a period ranging from about 1 to 24 hours.

12. The process according to claim 11 in which the tetranitro aryl ether compound is dissolved in a solvent; a catalyst and hydrazine or hydrazine hydrate are added to the resulting solution, said catalyst consisting essentially of palladium, platinum or Raney nickel on a charcoal support; and the solution is heated in an inert atmosphere under reflux conditions for a period of about 2 to 24 hours, thereby providing a reaction mixture containing a tetraamino aryl ether compound.

13. The process according to claim 12 in which the solvent is evaporated from the reaction mixture, thereby providing a solid tetraamino aryl ether compound.

14. The process according to claim 12 in which the reaction mixture is cooled; the cooled reaction mixture is mixed with concentrated hydrochloric acid, thereby precipitating hydrazine hydrochloride and a tetraamine hydrochloride aryl ether compound; the precipitate is dissolved in water; to the resulting solution a concentrated solution of ammonium hydroxide, sodium hydroxide, sodium carbonate or sodium bicarbonate is added, thereby precipitating a tetraamino aryl ether compound; and the tetraamino aryl ether compound is separated and dried.

* * * * *